(12) United States Patent  
Meier-Haack

(10) Patent No.: US 10,046,319 B2  
(45) Date of Patent: Aug. 14, 2018

(54) WATER-INSOLUBLE ANION EXCHANGER MATERIALS

(71) Applicant: LEIBNIZ-INSTITUT FUER POLYMERFORSCHUNG DRESDEN E.V., Dresden (DE)

(72) Inventor: Jochen Meier-Haack, Dresden (DE)

(73) Assignee: LEIBNIZ-INSTITUT FUER POLYMERFORSCHUNG DRESDEN E.V., Dresden (DE)

( * ) Notice: Subject to any disclaimer, the term of this patent is extended or adjusted under 35 U.S.C. 154(b) by 9 days.

(21) Appl. No.: 15/497,759

(22) Filed: Apr. 26, 2017

(65) Prior Publication Data

US 2017/0326540 A1 Nov. 16, 2017

(30) Foreign Application Priority Data

Apr. 27, 2016 (DE) .................. 10 2016 207 128

(51) Int. Cl.  
*B01J 41/12* (2017.01)  
*C08F 10/02* (2006.01)  
(Continued)

(52) U.S. Cl.  
CPC .............. *B01J 41/12* (2013.01); *C08F 10/02* (2013.01); *C08F 12/08* (2013.01); *C08F 14/26* (2013.01)

(58) Field of Classification Search  
USPC ......................................... 521/27; 525/328.2  
See application file for complete search history.

(56) References Cited

U.S. PATENT DOCUMENTS

2007/0225447 A1* 9/2007 Farnham ............... C08F 8/04  
525/328.2

FOREIGN PATENT DOCUMENTS

EP  2 351 785 A1   8/2011  
EP  2351785 A1 *  8/2011

OTHER PUBLICATIONS

Valade et al, "Preparation of Solid Alkaline Fuel Cell Binders Based on Fluorinated Poly(diallyldimethylammonium chloride)s [Poly(DADMAC)] or Poly(chlorotrifluoroethylene-co-DADMAC) Copolymers," J. Polym. Sci.: Part A: Polym. Chem. 47, 2009, 2043-2058.*

(Continued)

*Primary Examiner* — Mark Kaucher  
*Assistant Examiner* — Henry Hu  
(74) *Attorney, Agent, or Firm* — Greenblum & Bernstein, P.L.C.

(57) ABSTRACT

Water-insoluble anion exchange materials which exhibit improved insolubility in water are used, for example, for anion exchange membranes or as anion exchange resins. The water-insoluble anion exchange materials are at least composed of linearly polymerized and/or branched and/or crosslinked anion exchange groups C, which are part of the structural units according to at least one of the general formulas I to VIII:

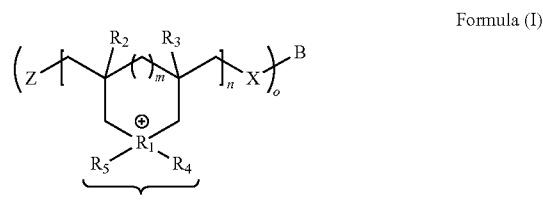

Formula (I)

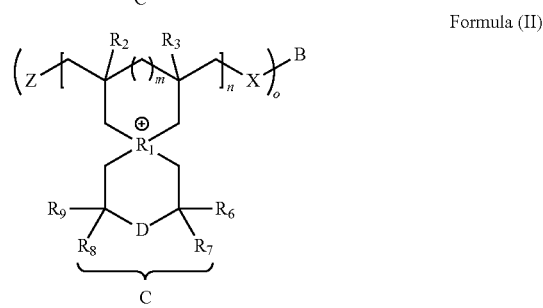

Formula (II)

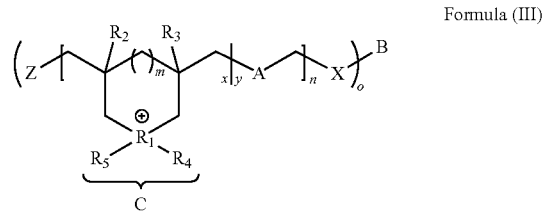

Formula (III)

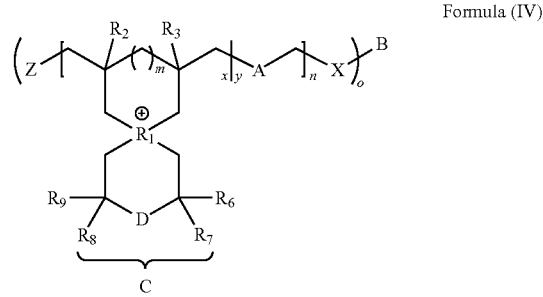

Formula (IV)

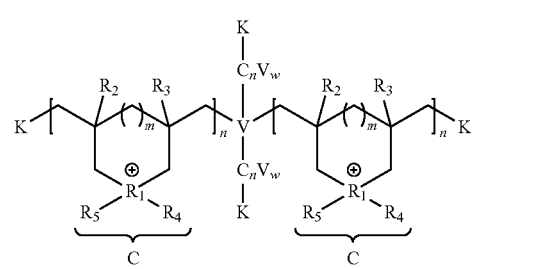

Formula (V)

(Continued)

-continued

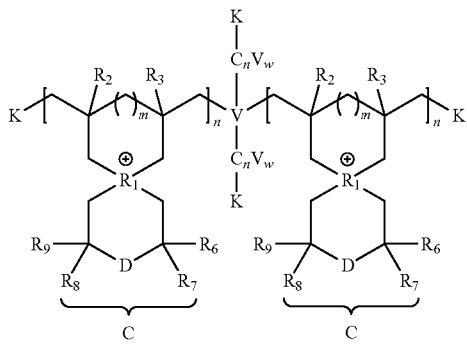

Formula (VI)

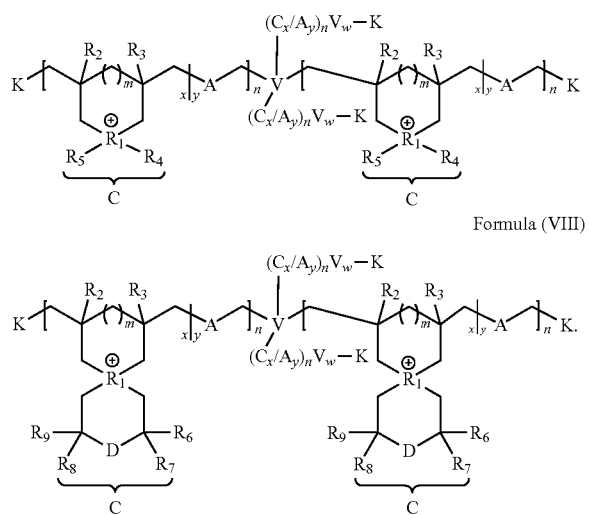

Formula (VII)

Formula (VIII)

18 Claims, No Drawings

(51) Int. Cl.
C08F 14/26 (2006.01)
C08F 12/08 (2006.01)

(56) References Cited

OTHER PUBLICATIONS

The Dow Chemical Company Product Data Sheet for Amberjet 9000 OH, Macroporous Strong Base Anion Exchange Resin, Form No. 177-02263-0411, Rev. 2, Aug. 2016.
The Dow Chemical Company Product Data Sheet for DOWEX Marathon A Resin, Uniform Particle Size, High Capacity, Strong Base Anion Exchange Resin, Form No. 177-02271-0311, Rev. 0.
The Dow Chemical Company Product Data Sheet for DOWEX Marathon C Resin, Uniform Particle Size, High Capacity Cation Exchange Resin, Form No. 177-02269-0311, Rev. 0.
Marino, M.G. and Kreuer, K.D., "Alkaline Stability of Quaternary Ammonium Cations for Alkaline Fuel Cell Membranes and Ionic Liquids" ChemSusChem 8, 2015, 513-523.
Pham, Thanh Huong, and Jannasch, Patric, "Aromatic Polymers Incorporating Bis-N-spirocyclic Quaternary Ammonium Moieties for Anion-Exchange Membranes," ACS Macro Letters 4 (2015) 1370-1375.
Hellwinkel and Seifert, "Zur Frage des pentakoordinierten Stickstoffs : Reaktionen von (spiro)cyclischen Tetraarylammonium-Salzen mit Nucleophilen," Liebigs Ann. Chem. 762 (1972) 29-54.
Qiao et al, "Anion conducting poly(vinyl alcohol)/poly(diallyldimethylammonium chloride) membranes with high durable alkaline stability for polymer electrolyte membrane fuel cells," J. Power Sources 237, 2013, 1-4.
de Vynck et al, "Synthesis and polymerization of N,N-diallylpyrrolidinium bromide," Macromol. Rapid Commun. 18, 1997, 149-156.

\* cited by examiner

WATER-INSOLUBLE ANION EXCHANGER MATERIALS

CROSS-REFERENCE TO RELATED APPLICATION

This application claims priority under 35 U.S.C. § 119(a) of German Patent Application No. 10 2016 207 128.9 filed Apr. 27, 2016, the disclosure of which is expressly incorporated by reference herein in its entirety.

The present invention concerns the field of polymer chemistry and relates to water-insoluble anion exchange materials as they are used, for example, for anion exchange membranes or as anion exchange resins for water treatment, in catalysts, for electrochemical processes such as electrodialysis or electrodeionization, or in energy converter systems such as fuel cells and reverse electrodialysis, or energy storage systems such as redox flow batteries.

Numerous anion exchange materials are known.

For example, known anion exchange resins are composed of cross-linked polystyrene, which resins comprise a benzyltrimethylammonium group as a functional group. For the use of anion exchange resins of this type in the OH form, operating temperatures between 35° C. and maximally 60° C. are specified (data sheet for Amberjet 9000 OH; data sheet for DOWEX Marathon A; data sheet for DOWEX Marathon 2; Dow Chemical Company).

The temperature stability of different low-molecular-weight quaternary ammonium salts in 6N NaOH at 160° C. was examined by Marino and Kreuer (ChemSusChem 8, 2015, 513-523). It was thereby discovered that the spirocyclic compound azoniaspiro[5.5]undecane exhibited the highest stability under the test conditions.

Aromatic anion exchange membranes based on polyethersulfones with N-spirocyclic ammonium groups are known from Pham and Jannasch, ACS Macro Letters 4 (2015) 1370-1375. The spirocyclic anion exchange groups are thereby condensed onto a phenyl ring and contain benzylic methylene groups.

Stability tests on these anion exchange membranes in 1M sodium hydroxide solution have shown a partial decomposition at only 40° C. after 168 h.

According to Hellwinkel and Seifert, bis-2,2'-biphenylene ammonium iodide exhibits a high thermostability in an alkaline medium, such as 20% sodium hydroxide solution, at boiling temperature. However, the synthesis of this compound is extremely costly, and the use thereof as a material for anion exchange membranes is therefore not economically reasonable (Liebigs Ann. Chem. 762 (1972) 29-54).

A copolymer of chlorotrifluoroethylene and diallyldimethylammonium chloride is specified by Valade et al. as a binder material for alkaline fuel cells (J. Polym. Sci.: Part A: Polym. Chem. 47, 2009, 2043-2205).

A disadvantage of this compound is that it cannot be used as a membrane material due to its low ion exchange capacity.

An anion exchange membrane based on a blend of poly(diallyldimethylammonium chloride) and polyvinyl alcohol is known from Qiao et al. (J. Power Sources 237, 2013, 1-4). To decrease water adsorption, the material was cross-linked with glutaraldehyde. After an initial loss of 55% of capacity, the ion exchange capacity of the membrane then remained stable in 8N potassium hydroxide solution within 375 hours.

The polymerization and structure of N,N-diallylpyrrolidinium bromide are known from de Vynck et al. (Macromol. Rapid Commun. 18, 1997, 149-156).

One disadvantage of the known solutions for anion exchange materials is that these materials are not yet sufficiently stable at temperatures above 50° C., in particular in an alkaline environment, and with regard to their insolubility in water.

The object of the invention is the specification of water-insoluble anion exchange materials that exhibit improved insolubility in water with simultaneously improved alkali and temperature stability, in particular at temperatures over 50° C.

The object is attained by the invention disclosed in the claims. Advantageous embodiments are the subject matter of the dependent claims.

The water-insoluble anion exchange materials are composed of at least linearly polymerized and/or branched and/or cross-linked anion exchange groups C, which form part of the structural units according to at least one of the general formulas I through VIII,

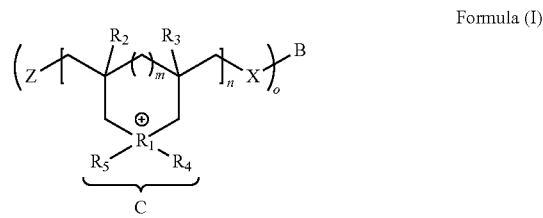

Formula (I)

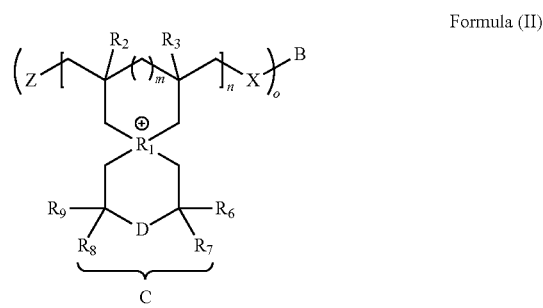

Formula (II)

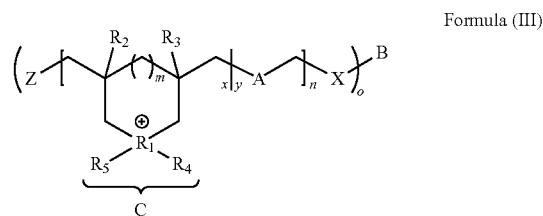

Formula (III)

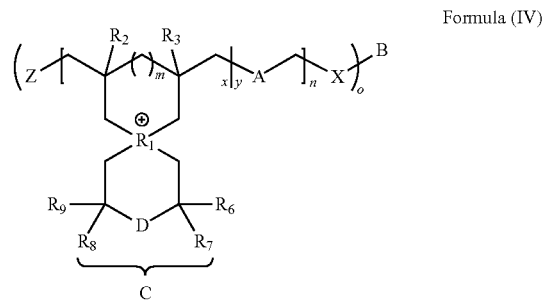

Formula (IV)

-continued

Formula (V)
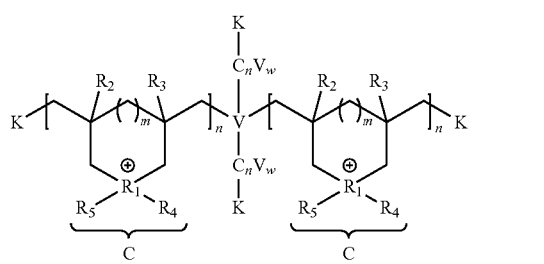

Formula (VI)
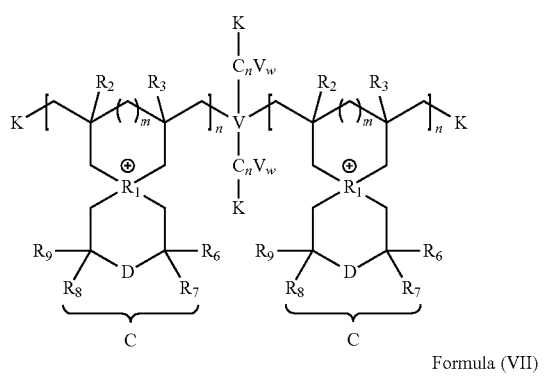

Formula (VII)
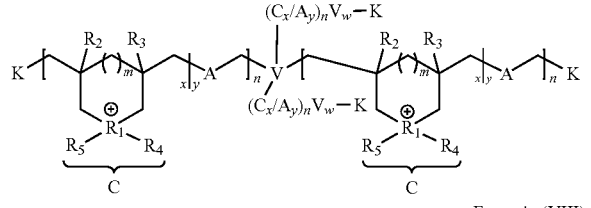

Formula (VIII)
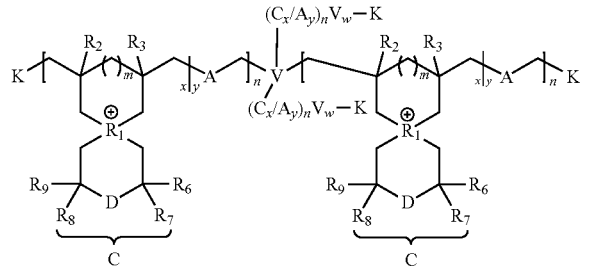

with
$R_1$ being nitrogen and/or phosphorus
$R_2$-$R_9$ being substituents, wherein
  $R_2$ and $R_3$ are hydrogen or, if at least one group $R_2$ and $R_3$ is not hydrogen, then $R_2$ and/or $R_3$ are an alkyl group or aryl group; and
  $R_4$ and $R_5$ are respectively an alkyl and/or aryl group; and
  $R_6$-$R_9$ are hydrogen, or if at least one group $R_6$ through $R_9$ is not hydrogen, then these groups $R_6$ through $R_9$ are an alkyl group or aryl group; and
Z is an end group; and
X is a connection point; and
V is a cross-linking point; and
K is an end group Z or a connection point X; and
D is nothing or is at least one methylene group or oxygen or sulfur; and
B is a water-insoluble temperature-stable and alkali-stable polymer; and A is a comonomer comprising no functional groups; and
$2 \leq n \leq 100$; and
$m = 0$ or $1$; and
$1 \leq o \leq 100$; and
50 mol % $\leq x \leq$ 99 mol % and y=(100 mol %−x); and
10 mol % $\leq w \leq$ 100 mol % and (n+w)=100 mol %;
wherein
in the case of K, at least one end group Z and at least one connection point X are present, and
the anion exchange groups C are coupled to a water-insoluble polymer B as a constituent of the structural units according to the general formulas I through IV via one, multiple or all connection points X, and essentially all end groups Z are a temperature- and alkali-stable compound;
and/or
the anion exchange groups C are cross-linked to one another as a constituent of the structural units according to the general formulas V through VIII via the cross-linking point V, and essentially all end groups Z are a temperature- and alkali-stable compound and all K that are a connection point X are coupled with a water-insoluble polymer B via covalent chemical bonds;
and/or
the anion exchange group C and the water-insoluble polymer B are connected via one or more ionic bonds.

Advantageously, at least two anion exchange groups C according to formulas I-IV are coupled one with another to a water-insoluble polymer B via a connection point X via covalent chemical bonds, and/or the anion exchange groups C are connected via ionic bonds to the water-insoluble polymer B and the end groups Z are temperature-stable and alkali-stable compounds.

Also advantageously, the connection point X is N,N-diallylpiperidinium ether or N,N-diallylpyrrolidinium ether or N,N-diallylaminoethyl ether or methacrylamidoethyl ether or methacrylic acid ester or methacrylic acid hydroxypropyl ether or xylylene ether or phenylene ether-sulfone.

Likewise advantageously, anion exchange groups C according to the formulas V through VIII are cross-linked via cross-linking points V, and K is a connection point X to which the water-insoluble polymer B is coupled via covalent chemical bonds.

Another advantageous embodiment is that the water-insoluble polymer B is connected via ionic bonds to the anion exchange groups C according to the general formulas I through VIII.

And also advantageously, the end groups Z are alkyl thioether or aryl thioether or benzyl thioether.

It is also advantageous if the water-insoluble, temperature-stable and alkali-stable polymer B is polyethersulfone or poly(thioether-sulfone) or polysulfone or polyphenylene or polyphenylene ether or polyphenylene sulfide or poly(perfluoroethylene-propylene) or polytetrafluoroethylene or poly(ethylene-tetrafluoroethylene) or perfluoroalkoxy polymers or polystyrene or polyethylene or polypropylene or a sulfonated and/or carboxylated and/or phosphonated polymer of the type polyethersulfone or polysulfone or polyphenylene or polyphenylene ether or polyphenylene sulfide or poly(perfluoroethylene-propylene) or polytetrafluoroethylene or poly(ethylene-tetrafluoroethylene) or perfluoroalkoxy polymers or polystyrene or polyethylene or polypropylene.

It is also advantageous if the comonomer A is styrene and/or α-methylstyrene and/or N-vinylcarbazole and/or methacrylic ester and/or N-vinylpyrrolidone and/or N,N-diallylacrylamide and/or N,N-diallylacrylsulfonamide and/or diallyl ether and/or 1,2-diallylbenzene and/or diallyl sulfide and/or chlorotrifluoroethylene and/or tetrafluoroethylene and/or hexafluoropropylene and/or 1,2-divinylbenzene.

It is likewise advantageous if the cross-linking point V is tetraallylammonium chloride or tetra(alkylallyl)ammonium chloride or diallyldi(alkylallyl)ammonium chloride or 1,4-divinylbenzene or divinyl sulfone or divinyl sulfide or divinylsulfoxide or divinyl ether or diacrylamide or dimethacrylamide or N,N,N',N'-tetraallyl-4,4'-trimethylenedipiperidinium chloride or N,N,N',N'-tetra(alkylallyl)-4,4'-trimethylenedipiperidinium chloride or N,N-diallyl-N',N'-di(alkylallyl)-4,4'-trimethylenedipiperidinium chloride or N-allyl-N,N',N'-tri(alkylallyl)-4,4'-trimethylenedipiperidinium chloride or N,N,N'-triallyl-N'-(alkylallyl)-4,4'-trimethylenedipiperidinium chloride or N,N,N',N'-tetraallylpiperazinium chloride, N,N,N',N'-tetra(alkylallyl)piperazinium chloride or N,N-diallyl-N',N'-di(alkylallyl)piperazinium chloride or N-allyl-N,N',N'-tri(alkylallyl)piperazinium chloride or N,N,N'-triallyl-N'-(alkylallyl)piperazinium chloride and/or a bromide and/or an iodide of these compounds.

It is further advantageous if N,N-diallyl and/or N,N-di(alkylallyl) compounds and/or N-allyl-N-(alkylallyl) compounds of secondary aliphatic or aromatic or cycloaliphatic amines, such as for example diallyldimethylammonium chloride, diallylpiperidinium chloride, diallylpyrrolidinium chloride, allylmethallyldimethylammonium chloride, allylmethallylpiperidinium chloride, allylmethallylpyrrolidinium chloride, dimethallyldimethylammonium chloride, dimethallylpiperidinium chloride, dimethallylpyrrolidinium chloride diallyl-3,4-dimethylpyrrolidinium chloride, diallyl-3,3,4,4-tetramethylpyrrolidinium chloride, diallyl-3,5-dimethylpiperidinium chloride, diallyl-3,3,5,5-tetramethylpiperidinium chloride, diallyldiphenylammonium chloride, P,P-diallyl compounds and/or P,P-di(alkylallyl) compounds and/or P-allyl-P-(alkylallyl) compounds of secondary aliphatic or aromatic or cycloaliphatic phosphines, such as for example diallyldimethylphosphonium chloride, diallyldiphenylphosphonium chloride and/or a bromide and/or an iodide of these compounds are used as monomers for the production of the anion exchange groups C.

It is also advantageous if $R_1$ is nitrogen.

Additionally, it is advantageous if $R_2$ and/or $R_3$ are a methyl group and/or hydrogen.

Likewise, it is advantageous if $R_4$ and $R_5$ are an alkyl group and are advantageously a methyl or ethyl group.

It is furthermore advantageous if $R_6$-$R_9$ are hydrogen.

And it is also advantageous if $10 \leq n \leq 50$.

Additionally, it is advantageous if $2 \leq o \leq 10$.

With the present invention, it is for the first time possible to specify water-insoluble materials for anion exchange membranes which exhibit an improved alkali and temperature stability, in particular at temperatures over 50° C.

This is attained by water-insoluble anion exchange materials, at least composed of linearly polymerized and/or branched and/or cross-linked anion exchange groups C, which are part of the structural units according to at least one of the general formulas I through VIII,

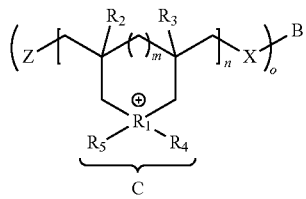

Formula (I)

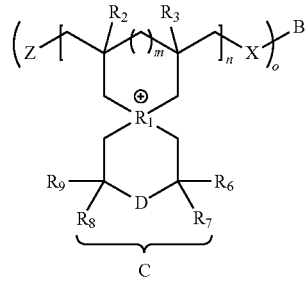

Formula (II)

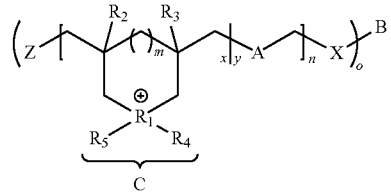

Formula (III)

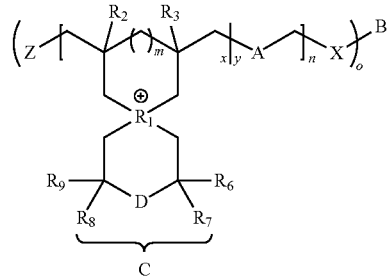

Formula (IV)

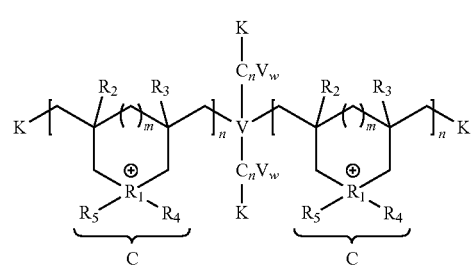

Formula (V)

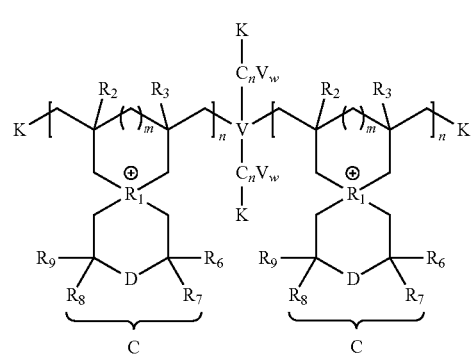

Formula (VI)

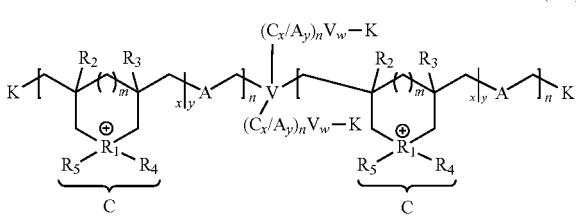

Formula (VII)

-continued

Formula (VIII)

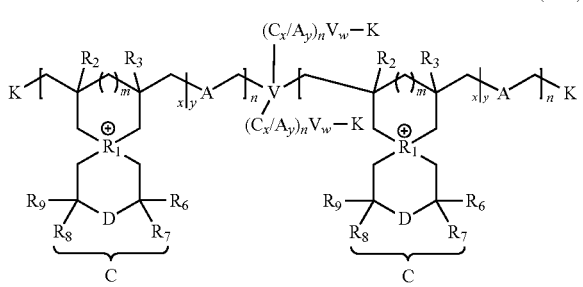

with
R$_1$ being nitrogen and/or phosphorus
R$_2$-R$_9$ being substituents, wherein
  R$_2$ and R$_3$ are hydrogen or, if at least one group R$_2$ and R$_3$ is not hydrogen, then R$_2$ and/or R$_3$ are an alkyl group or aryl group; and
  R$_4$ and R$_5$ are respectively an alkyl and/or aryl group; and
  R$_6$-R$_9$ are hydrogen, or if at least one group R$_6$ through R$_9$ is not hydrogen, then these groups R$_6$ through R$_9$ are an alkyl group or aryl group;
and
Z is an end group; and
X is a connection point; and
V is a cross-linking point; and
K is an end group Z or a connection point X; and
D is nothing or is at least one methylene group or oxygen or sulfur; and
B is a water-insoluble polymer; and
A is a comonomer comprising no functional groups; and
$2 \leq n \leq 100$; and
$m = 0$ or 1; and
$1 \leq o \leq 100$; and
50 mol % $\leq x \leq 99$ mol % and y=(100 mol %–x); and
10 mol % $\leq w \leq 100$ mol % and (n+w)=100 mol %.
It is essential to the invention that
in the case of K, at least one end group Z and at least one connection point X are present, and
the anion exchange groups C are coupled to a water-insoluble polymer B as a constituent of the structural units according to the general formulas I through IV via one, multiple or all connection points X, and essentially all end groups Z are a temperature- and alkali-stable compound;
and/or
the anion exchange groups C are cross-linked to one another as a constituent of the structural units according to the general formulas V through VIII via the cross-linking point V, and essentially all end groups Z are a temperature- and alkali-stable compound and all K that are a connection point X are coupled with a water-insoluble polymer B via covalent chemical bounds;
and/or
the anion exchange groups C and the water-insoluble polymer B are connected via one or more ionic bonds.

The water-insoluble anion exchange materials according to the invention thus comprise a linearly polymerized and/or branched and/or cross-linked structure.

Thereby, the anion exchange groups C can be both only linearly polymerized with one another and/or with compounds and/or branched and/or also three-dimensionally cross-linked. This means that if only structural units according to the general formulas I to IV are present, they can only be coupled in a linearly chemical and/or branched manner. Branched compounds of the anion exchange groups should be linearly polymerized compounds with side chains which essentially lack chemical coupling among one another.

In the case that structural units according to the general formulas V to VIII are present, linear parts are also present in the structural units, which may also be branched, depending on the length of the structural units used, but at the crosslinking points the structural units according to the general formula Formulas V to VIII are always three-dimensionally chemically coupled and thus cross-linked.

The structural units according to the general formulas I through VIII are in each case coupled with water-insoluble, preferably aromatic or aliphatic and inert under use conditions, polymers B, wherein the anion exchange groups C are coupled at least at one end of the polymers B via the connection point X and/or via K, where K is equal to X. The other end of the polymer chain is formed by the end group Z or K, which is a temperature- and alkali-stable compound, preferably a low-molecular-weight aromatic or aliphatic compound that is inert under use conditions.

For the structural units according to the general formulas V through VIII, the anion exchange groups C are chemically coupled to one another three-dimensionally, that is, cross-linked, via the cross-linking points V, wherein essentially at the respective ends of the polymer chains, also on possible side groups, K are present in a coupled manner as end groups Z, which are a temperature-stable and alkali-stable compound, advantageously a low-molecular-weight or aromatic or aliphatic compound that is inert under use conditions.

In the case of structural units according to the general formulas V through VIII, according to the invention at least one K is a connection point X that is present in a coupled manner with water-insoluble, advantageously aromatic or aliphatic and inert under use conditions, polymers B, wherein simultaneously at least one K represents an end group Z that is not present in a coupled manner with water-insoluble, advantageously aromatic or aliphatic and inert under use conditions, polymers B.

Advantageously, more K are connection points X that are coupled with water-insoluble, advantageously aromatic or aliphatic and inert under use conditions, polymers B than K that are not coupled with water-insoluble, advantageously aromatic or aliphatic and inert under use conditions, polymers B. If K is an end group Z, however, then it is not coupled with polymer B.

Alkylthio ether or arylthio ether or benzylthio ether can advantageously be present as end groups Z.

The connection point X can advantageously be N,N-diallylpiperidinium ether or N,N-diallylpyrrolidinium ether or N,N-diallylaminoethyl ether or methacrylamidoethyl ether or methacrylic acid ester or methacrylic acid hydroxypropyl ether or xylylene ether or phenylenesulfone ether.

For the connection point X, one, multiple or all connection points X are coupled with their respective partner via covalent chemical bonds. Advantageously, the majority of connection points X are coupled with their partners via covalent chemical bonds.

In the anion exchange materials according to the invention, the coupling between the anion exchange groups C according to the general formulas I through VIII and the water-insoluble polymer B can also occur via ionic bonds between the anion exchange groups C and acidic groups of the polymers B.

The cross-linking point V is advantageously tetraallylammonium chloride or tetra(alkylallyl)ammonium chloride or diallyldi(alkylallyl)ammonium chloride or 1,4-divinylbenzene or divinylsulfone or divinyl sulfide or divinylsulfoxide or divinyl ether or diacrylamide or dimethacrylamide or N,N,N',N'-tetraallyl-4,4'-trimethylenedipiperidinium chloride or N,N,N',N'-tetra(alkylallyl)-4,4'-trimethylenedipiperidinium chloride or N,N-diallyl-N',N'-di(alkylallyl)-4,4'- trimethylenedipiperidinium chloride or N-allyl-N,N',N'-tri (alkylallyl)-4,4'-trimethylenedipiperidinium chloride or N,N,N'-triallyl-N'-(alkylallyl)trimethylenedipiperidinium chloride or N,N,N',N'-tetraallylpiperazinium chloride or N,N,N',N'-tetra(alkylallyl)piperazinium chloride or N,N-diallyl-N',N'-di(alkylallyl)piperazinium chloride or N-allyl-N,N',N'-tri(alkylallyl)piperazinium chloride or N,N,N'-triallyl-N'-(alkylallyl)piperazinium chloride. In place of the aforementioned ammonium chlorides, the bromides or iodides thereof can also be used.

If D is nothing and/or m=0 this means, within the scope of the present invention, that the cyclic structural element of the anion exchange group C is a five-membered ring.

The water-insoluble polymer B, which advantageously is also temperature- and/or alkali-stable, is advantageously polyethersulfone or polysulfone or polyphenylene or polyphenylene ether or polyphenylene sulfide or poly(perfluoroethylene-propylene) or polytetrafluoroethylene or poly(ethylene-tetrafluoroethylene) or perfluoroalkoxy polymers or polystyrene or polyethylene or polypropylene.

Likewise advantageously, the comonomer A is styrene and/or α-methylstyrene and/or N-vinylcarbazole and/or methacrylic ester and/or N-vinylpyrrolidone and/or N,N-diallylacrylamide and/or N,N-diallylacrylsulfonamide and/or diallyl ether and/or 1,2-diallylbenzene and/or diallyl sulfide and/or chlorotrifluoroethylene and/or tetrafluoroethylene and/or hexafluoropropylene and/or 1,2-divinylbenzene.

The comonomer A is thereby advantageously present for the spatial separation of charge-carrying groups.

Advantageously $R_1$ is nitrogen, $R_6$ through $R_9$ are hydrogen, $R_2$ and/or $R_3$ are hydrogen or a methyl group, and $R_4$ and/or $R_5$ are a methyl group or ethyl group.

The water-insoluble anion exchange materials according to the invention are attained in that the nitrogen- or phosphorus-containing anion exchange groups C of the water-insoluble anion exchange materials according to the invention are integrated in the cyclic (heterocyclic) or spirocyclic compounds of the structural units according to at least one of the general formulas I through VIII.

In addition, β-position hydrogen atoms for the positively charged atom of the anion exchange groups C in the structural units according to at least one of the general formulas I through VIII can be substituted by alkyl or aryl groups.

By integrating the anion exchange groups C into the structural units according to at least one of the general formulas I through VIII as segments in linear block copolymers that also have a brush-like shape as a result of polymerized side chains, or by producing three-dimensionally cross-linked polymers therefrom and the presence of end groups Z (K=Z in the formulas V through VIII) and the coupling via connection points X (K=X in the formulas V through VIII) with water-insoluble polymers B, the water-insoluble anion exchange materials are present.

The improved alkali and temperature stability of the water-insoluble materials according to the invention allows the development of new fields of application or an improved efficiency in known applications.

The water-insoluble anion exchange materials according to the invention can be used for anion exchange membranes or what are referred to as anion exchange resins. The anion exchange membranes are thereby composed essentially, but at least mostly, of linear anion exchange groups C that are a constituent of the structural units according to at least one of the general formulas I through IV. Anion exchange resins are composed essentially, but at least mostly, of cross-linked anion exchange groups C that are a constituent of the structural units according to at least one of the general formulas V through VIII.

Another advantageous property of the water-insoluble anion exchange materials according to the invention is their odorlessness.

The water-insoluble anion exchange materials according to the invention are produced by means of cyclopolymerization.

Advantageously, N,N-diallyl and/or N,N-di(alkylallyl) compounds and/or N-allyl-N-(alkylallyl) compounds of secondary aliphatic or aromatic or cycloaliphatic amines, such as for example diallyldimethylammonium chloride, diallylpiperidinium chloride, diallylpyrrolidinium chloride, allylmethallyldimethylammonium chloride, allylmethallylpiperidinium chloride, allylmethallylpyrrolidinium chloride, dimethallyldimethylammonium chloride, dimethallylpiperidinium chloride, dimethallylpyrrolidinium chloride, diallyl-3,4-dimethylpyrrolidinium chloride, diallyl-3,3,4,4-tetramethylpyrrolidinium chloride, diallyl-3,5-dimethylpiperidinium chloride, diallyl-3,3,5,5-tetramethylpiperidinium chloride, diallyldiphenylammonium chloride, are used as monomers for the production of the anion exchange groups C. Likewise advantageously P,P-diallyl and/or P,P-di(alkylallyl) compounds and/or P-allyl-P-(alkylallyl) compounds of secondary aliphatic or aromatic or cycloaliphatic phosphines, such as for example diallyldimethylphosphonium chloride, diallyldiphenylphosphonium chloride can be used as monomers of this type. In place of the ammonium chlorides or phosphonium chlorides, the corresponding bromides or iodides can also be used.

The water-insoluble anion exchange materials according to the invention exhibit a considerably higher temperature stability, in particular under alkaline conditions, than materials of comparable membranes according to the prior art. Therefore, the anion exchange materials according to the invention can be used in the existing areas of application for materials of this type without a problem, and can thus lead to an improvement in the efficiency of these methods. As a result of the improved properties, new fields of application for the materials according to the invention can also present themselves.

The invention is explained below in greater detail with the aid of two exemplary embodiments:

EXAMPLE 1

Production of an anion exchange membrane from multiple anion exchange groups C of the structural unit according to the general formula II with coupling via a water-insoluble polymer B For the production of the anion exchange membrane, the water-insoluble polymer B was first produced. To do so, 52 mmol 4,4-difluorodiphenyl sulfone and 50 mmol 4,4'-bis-trimethylsiloxydiphenylsulfone were dissolved in 50 mL N-methylpyrrolidone (NMP) and subsequently mixed with 75 mmol potassium carbonate. This mixture was stirred at 175° C. under an argon atmosphere for 16 h. Then, the temperature was increased to 190° C. for 2 hours, and an additional 100 mg 4,4'-difluorodiphenyl sulfone was added. After cooling down, the product of the reaction was precipitated in 1000 mL ethanol with the addition of 5 mL 37% hydrochloric acid. This product was filtered off and washed with 250 mL ethanol at 50° C. for 5 h, filtered off, and dried under vacuum at 100° C. The end product was a fluorine-terminated polyethersulfone (polymer B) having a molecular weight $M_n$, determined by $^1$H-NMR spectroscopy, of 11,000 g/mol and containing no OH end groups.

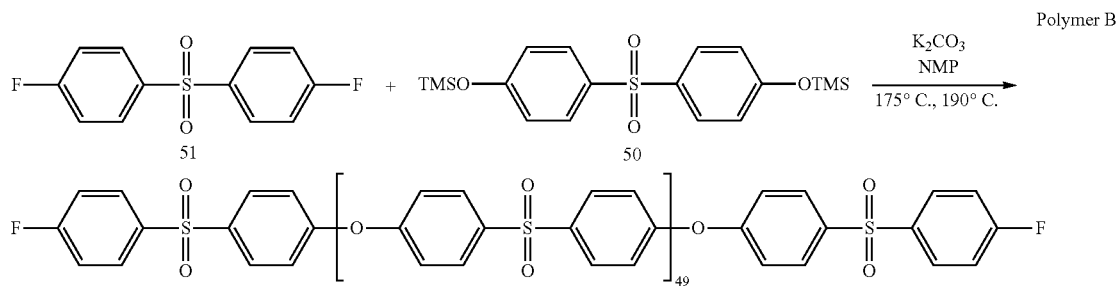

For the production of the connection points X at the polymer B according to the reaction illustrated below, 2 mmol polyether sulfone and 4 mmol 4-hydroxypiperidine were dissolved in 50 mL NMP and mixed with 6 mmol potassium carbonate. This initial solution was stirred at 175° C. for 16 h, and the intermediate product was then precipitated with 500 mL ethanol. The polymer obtained thereby was stirred in ethanol at 50° C. for 5 h, filtered off, and dried under vacuum at 100° C.

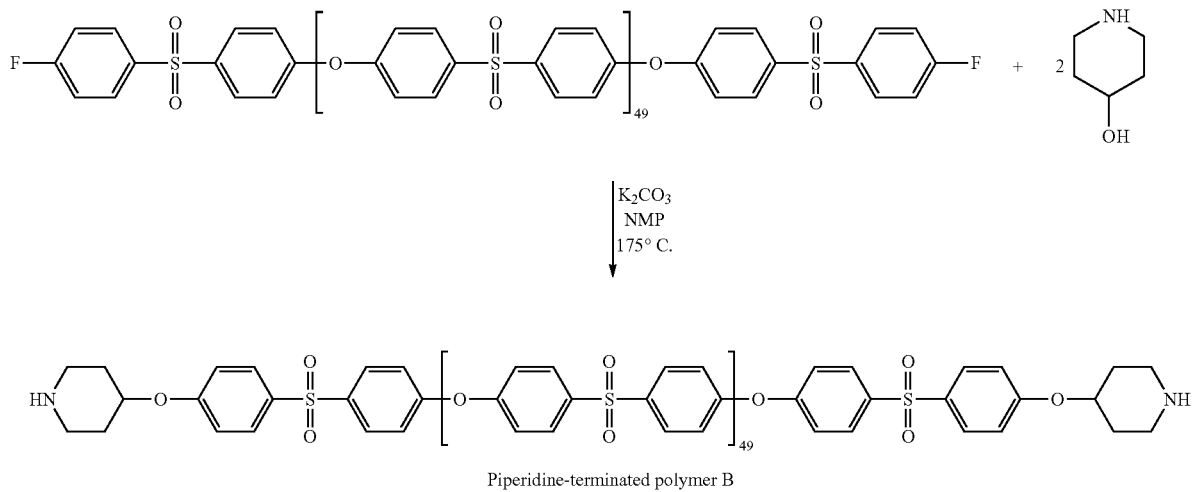

The final product was a piperidine-terminated polyethersulfone. The yield was 90%. The complete reaction of the fluoro end groups with 4-hydroxypiperidine was verified by means of $^1$H-NMR spectroscopy.

0.5 mmol of this piperidine-terminated polyethersulfone was dissolved in 25 mL dimethyl sulfoxide (DMSO) and mixed with 4 mmol potassium carbonate and heated to 75° C. Over a period of 30 min, 4 mmol allyl chloride, dissolved in 10 mL DMSO, was dropped into the reaction mixture.

After the allyl chloride dissolved in DMSO was fully added, the mixture was stirred at 90° C. for 24 h. After cooling down, the polyethersulfone that was diallylpiperidinium-terminated with the connection point X was precipitated in ethanol, stirred in fresh ethanol at 50° C., and subsequently filtered off. The product was dried under vacuum at 50° C. The yield was 85%. The complete formation of the terminal quaternary ammonium salts was established by means of $^1$H-NMR spectroscopy.

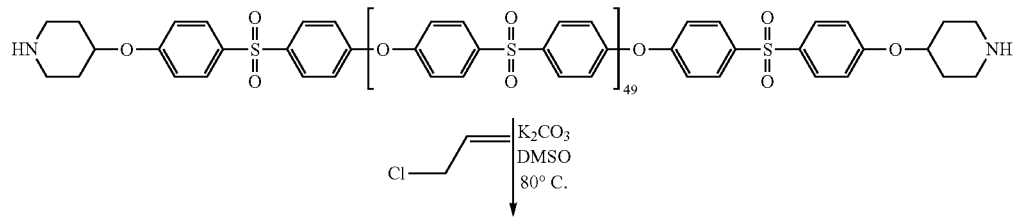

-continued

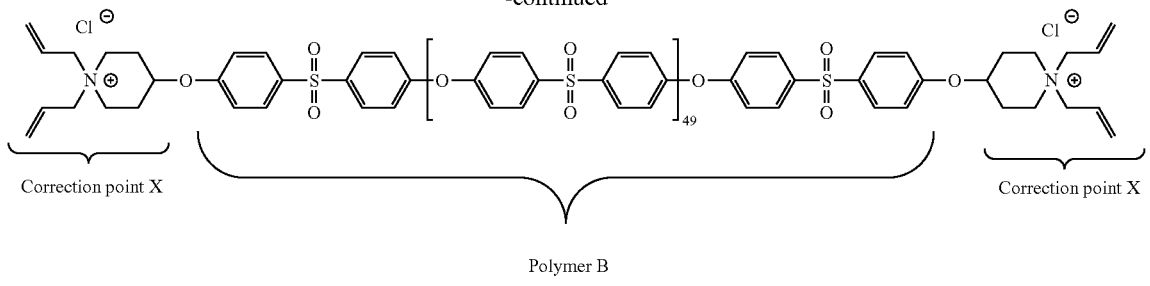

Polymer B

Polymer B with connection points X

Afterwards, for the production of the compound with multiple anion exchange groups C, according to the structural unit from the general formula II, 0.1 mmol of the diallylpiperidinium-terminated polyethersulfone (polymer B with connection points X) and 4 mmol N,N-diallylpyrrolidinium chloride (anion exchange group C according to formula II, produced analogously to the specification according to de Vynck et al., Macromol. Rapid Commun. 18, 1997, 149-156) were dissolved in 50 mL DMSO and freed of dissolved oxygen by means of four freeze/thaw cycles. The reaction solution was heated to 90° C. and mixed with 4 mol % AIBN, stirred at 90° C. under an argon atmosphere for 24 h. After cooling down, the resulting polyethersulfone poly(azoniaspiro[4,4]nonane) block polymer was treated with thiophenol in the presence of copper(I) salt for the purpose of saturation of the terminal double bonds and subsequently precipitated in water. Any homopolymer possibly produced during the reaction was removed by extraction with water in a Soxhlet apparatus. The composition, which was determined by means of $^1$H-NMR spectroscopy, corresponded to the monomer composition according to formula II. The yield was 95%.

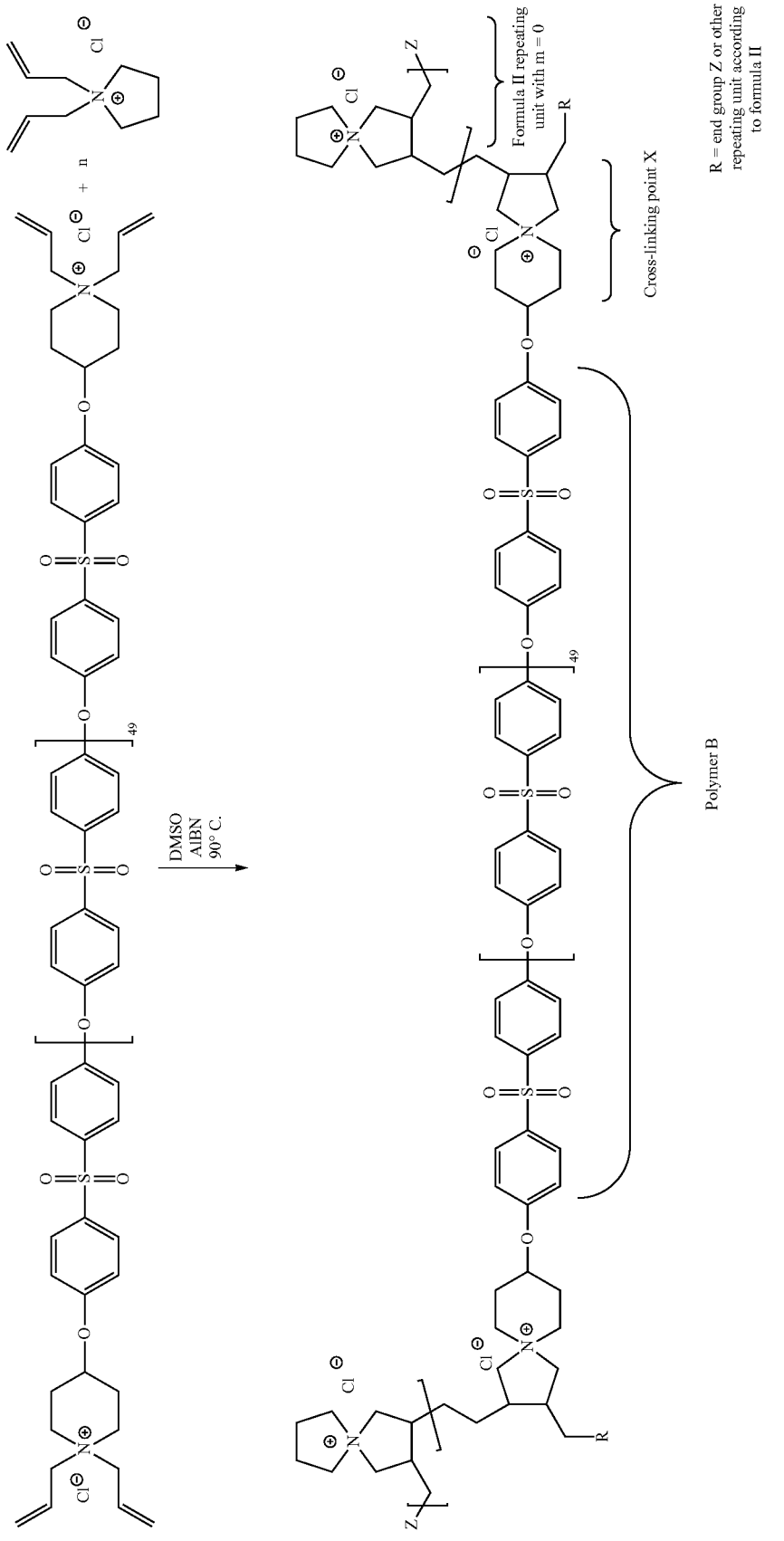

From the polyethersulfone poly(azoniaspiro[4,4]nonane) block polymer produced in this manner, a membrane was then produced. To do so, 0.5 g polyethersulfone poly(azoniaspiro[4,4]nonane) block polymer was dissolved in 10 mL N-methylpyrrolidone, filtered, and poured into a Petri dish with a diameter of 7 cm. The solvent N-methylpyrrolidone was removed under vacuum at room temperature for 2 h, subsequently at 40° C. for 2 h, at 60° C. for an additional 2 h, and then at 100° C. for 24 h. The resulting membrane was removed from the Petri dish using water, washed in water at 70° for 4 h, and finally dried under vacuum at 50° C. until reaching constant weight.

The membrane of polyethersulfone poly(azoniaspiro[4,4]nonane) block copolymer had a thickness (dry) of 70 μm, an ion exchange capacity=1.30 mmol/g, a water absorption at 80° C.=65%, and a hydroxide ion conductivity (80° C., 95% relative humidity)=70 mS/cm.

The membrane material polyethersulfone poly(azoniaspiro[4,4]nonane) block copolymer was characterized with regard to its temperature stability. To do so, 0.5 g of the membrane of polyethersulfone poly(azoniaspiro[4,4]nonane) block copolymer was initially stored in 2M sodium hydroxide solution for 24 hours in order to convert the anion exchange material into the OH form. The membrane was then added to 5 mL 2N sodium hydroxide solution, the vessel was fused, and the contents were kept at a temperature of 120° C. for 168 h. After cooling down the vessel was opened, and the anion exchange material was washed with water and subsequently stored in 1M sodium chloride solution for 24 h. The sample was once again washed with water, and dried under vacuum at 50° C. until reaching constant weight.

The membrane material thereby showed the following results, wherein the values in each case were established before and after determining the temperature stability.

Mass
before test=0.5 g, after test=0.49 g,
Ion exchange capacity
before test=1.30 mmol/g, after test=1.29 mmol/g,
Hydroxide ion conductivity (80° C., 95% relative humidity)
before test=70 mS/cm, after test=69 mS/cm.

The differences in the results lie within the margin of error for each measuring procedure.

EXAMPLE 2

Production of an anion exchange membrane from a cross-linked compound with multiple anion exchange groups C that are a constituent of the structural units according to the general formula VI with coupling via a water-insoluble polymer B For the production of the anion exchange membrane, the water-insoluble polymer B was first produced with K, which represents a connection point X, according to Example 1. A solution of 0.1 mmol polymer B, 10 mmol N,N-diallylpiperidinium chloride and 2 mmol N,N,N,N-tetraallylammonium chloride as a cross-linking point V and 0.1 mmol 2,4,6-trimethylbenzoyl diphenylphosphine oxide (DPO) as a UV initiator were dissolved in 10 mL dimethylsulfoxide and carefully degassed. This solution was poured into a Petri dish with a diameter of 7 cm, which was covered with a quartz glass disc and irradiated with UV light at a wavelength of 254 nm (output power of 8 W) at room temperature for 10 min. The solvent was then removed under vacuum at a temperature of 100 to 120° C. The anion exchange material was washed with water and treated with thiophenol in the presence of copper(I) salt for the saturation of the terminal double bonds. The anion exchange membrane was once again thoroughly washed with water, and dried under vacuum until reaching constant weight. The membrane had a thickness of 100 μm (dry), an ion exchange capacity of 3.35 mmol/g, a water absorption at 80° C. of 100%, and a hydroxide ion conductivity (80° C., 95% relative humidity) of 90 mS/cm.

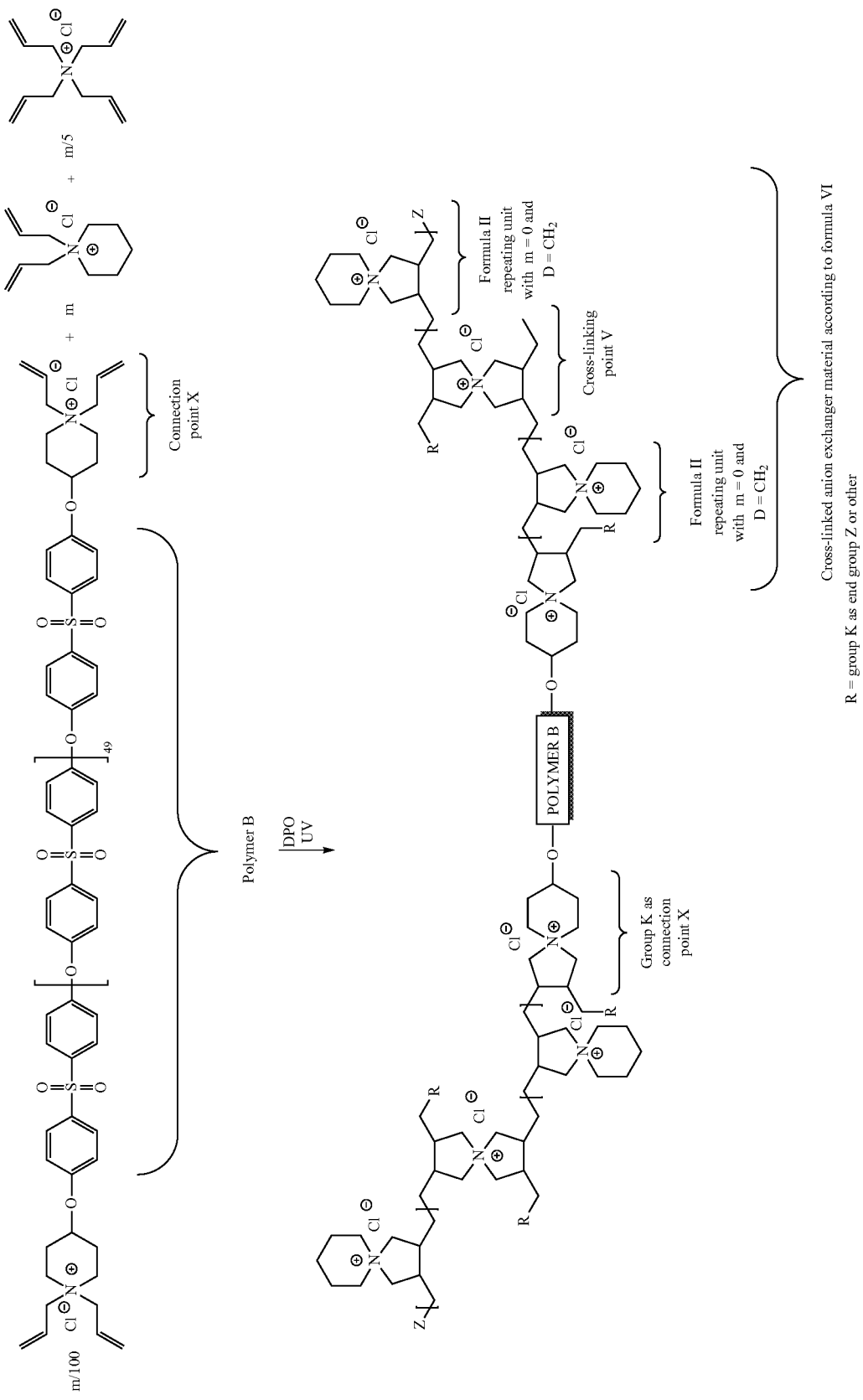

The membrane material was characterized with regard to its temperature stability. To do so, 0.5 g of the membrane was first stored in 2M sodium hydroxide solution for 24 hours in order to convert the anion exchange material into the OH form. The membrane was then added to 5 mL 2N sodium hydroxide solution, the vessel was fused, and the contents were kept at a temperature of 120° C. for 168 h. After cooling down the vessel was opened, and the anion exchange material was washed with water and subsequently stored in 1M sodium chloride solution for 24 h. The sample was once again washed with water, and dried under vacuum at 50° C. until reaching constant weight.

The membrane material thereby showed the following results, wherein the values in each case were established before and after determining the temperature stability.

Mass before test=0.5 g, after test=0.49 g,

Ion exchange capacity before test=3.35 mmol/g, after test=3.32 mmol/g,

Hydroxide ion conductivity (80° C., 95% relative humidity)

before test=90 mS/cm, after test=88 mS/cm.

The differences in the results lie within the margin of error for each measuring procedure.

The invention claimed is:

1. Water-insoluble anion exchange materials comprising at least linearly polymerized and/or branched and/or crosslinked anion exchange groups C, which form part of the structural units according to at least one of the general formulas I to VIII,

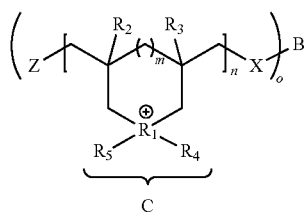

Formula (I)

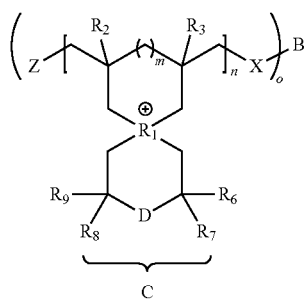

Formula (II)

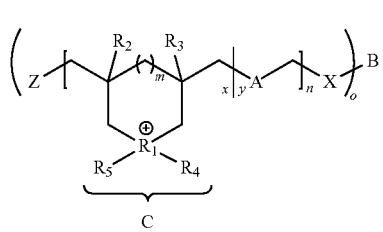

Formula (III)

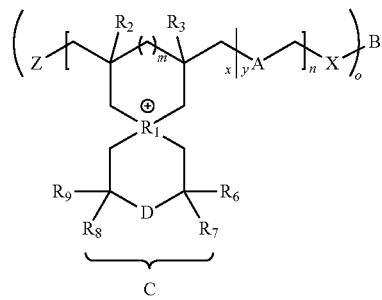

Formula (IV)

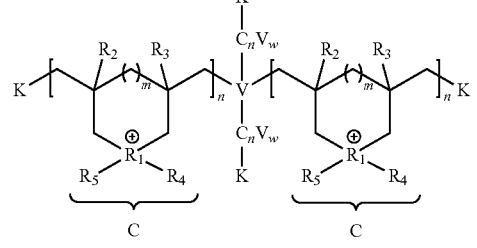

Formula (V)

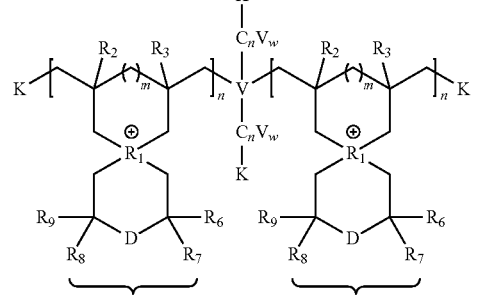

Formula (VI)

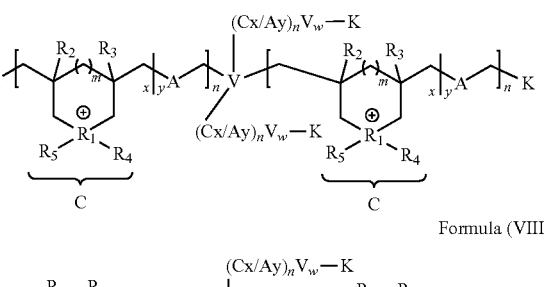

Formula (VII)

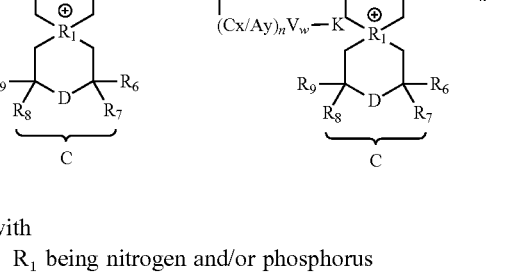

Formula (VIII)

with $R_1$ being nitrogen and/or phosphorus $R_2$-$R_9$ being substituents, wherein $R_2$ and $R_3$ are hydrogen or, if at least one group $R_2$ and $R_3$ is not hydrogen, then $R_2$ and/or $R_3$ are an alkyl group or aryl group; and R$_4$ and R$_5$ are respectively an alkyl and/or aryl group; and R$_6$-R$_9$ are hydrogen, or if at least one group R$_6$ through R$_9$ is not hydrogen, then these groups R$_6$ through R$_9$ are an alkyl group or aryl group; and Z is an end group; and X is a connection point; and V is a cross-linking point; and K is an end group Z or a connection point X; and D is nothing or is at least one methylene group or oxygen or sulfur; and B is a water-insoluble temperature-stable and alkali-stable polymer; and A is a comonomer comprising no functional groups; and $2 \leq n \leq 100$; and m=0 or 1; and $1 \leq o \leq 100$; and 50 mol %$\leq$x$\leq$99 mol % and y=(100 mol %–x); and 10 mol %$\leq$w$\leq$100 mol % and (n+w)=100 mol %;

wherein in the case of K, at least one end group Z and at least one connection point X are present, and
the anion exchange groups C are coupled to a water-insoluble polymer B as a constituent of the structural units according to the general formulas I through IV via one, multiple or all connection points X, and essentially all end groups Z are a temperature- and alkali-stable compound;

and/or the anion exchange groups C are cross-linked to one another as a constituent of the structural units according to the general formulas V through VIII via the cross-linking point V, and essentially all end groups Z are a temperature- and alkali-stable compound and all K that are a connection point X are coupled with a water-insoluble polymer B via covalent chemical bounds;

and/or the anion exchange group C and the water-insoluble polymer B are connected via one or more ionic bonds.

2. The water-insoluble anion exchange materials according to claim 1, in which at least two anion exchange groups C according to formula I-IV are coupled one with another to a water-insoluble polymer B via a connection point X via covalent chemical bonds, and/or the anion exchange groups C are connected via ionic bonds to the water-insoluble polymer B and the end groups Z are temperature-stable and alkali-stable compounds.

3. The water-insoluble anion exchange materials according to claim 1, in which the connection point X is N,N-diallylpiperidinium ether or N,N-diallylpyrrolidinium ether or N,N-diallylaminoethyl ether or methacrylamidoethyl ether or methacrylic acid ester or methacrylic acid hydroxypropyl ether or xylylene ether or phenylene ether-sulfone.

4. The water-insoluble anion exchange materials according to claim 1, in which anion exchange groups C according to formula V through VIII are cross-linked via cross-linking points V, and K is a connection point X to which the water-insoluble polymer B is coupled via covalent chemical bonds.

5. The water-insoluble anion exchange materials according to claim 1, in which the end groups Z are alkylthio ether or arylthio ether or benzylthio ether.

6. The water-insoluble anion exchange materials according to claim 1, in which the water-insoluble, temperature-stable and alkali-stable polymer B is polyethersulfone or polysulfone or poly(thioether-sulfone) or polyphenylene or polyphenylene ether or polyphenylene sulfide or poly(perfluoroethylene-propylene) or polytetrafluoroethylene or poly(ethylene-tetrafluoroethylene) or perfluoroalkoxy polymers or polystyrene or polyethylene or polypropylene or a sulfonated and/or carboxylated and/or phosphonated polymer of the type polyethersulfone or polysulfone or polyphenylene or polyphenylene ether or polyphenylene sulfide or poly(perfluoroethylene-propylene) or polytetrafluoroethylene or poly(ethylene-tetrafluoroethylene) or perfluoroalkoxy polymers or polystyrene or polyethylene or polypropylene.

7. The water-insoluble anion exchange membrane according to claim 1, in which the comonomer A is styrene and/or α-methylstyrene and/or N-vinylcarbazole and/or methacrylic ester and/or N-vinylpyrrolidone and/or N,N-diallylacrylamide and/or N,N-diallylacrylsulfonamide and/or diallyl ether and/or 1,2-diallylbenzene and/or diallyl sulfide and/or chlorotrifluoroethylene and/or tetrafluoroethylene and/or hexafluoropropylene and/or 1,2-divinylbenzene.

8. The water-insoluble anion exchange materials according to claim 1, in which the cross-linking point V is tetraallylammonium chloride or tetra(alkylallyl)ammonium chloride or diallyldi(alkylallyl)ammonium chloride or 1,4-divinylbenzene or divinylsulfone or divinyl sulfide or divinylsulfoxide or divinyl ether or diacrylamide or dimethacrylamide or N,N,N',N'-tetraallyl-4,4'-trimethylenedipiperidinium chloride or N,N,N',N'-tetra(alkylallyl)-4,4'-trimethylenedipiperidinium chloride or N,N-diallyl-,N',N'-(dialkylallyl)-4,4'-trimethylenedipiperidinium chloride or N-allyl-N,N',N'-tri(alkylallyl)-4,4'-trimethylenedipiperidinium chloride or N,N,N'-triallyl-N'-(alkylallyl)-4,4'-trimethylenedipiperidinium chloride or N,N,N',N'-tetraallylpiperazinium chloride or N,N,N',N'-tetra(alkylallyl)piperazinium chloride or N,N'-diallyl-N',N'-di(alkylallyl)piperazinium chloride or N-allyl-N,N',N'-tri(alkylallyl)piperazinium chloride or N,N,N'-triallyl-N'-(alkylallyl)piperazinium chloride and/or a bromide and/or an iodide of these compounds.

9. The water-insoluble anion exchange materials according to claim 1, in which N,N-diallyl and/or N,N-di(alkylallyl) compounds and/or N-allyl-N-(alkylallyl) compounds of secondary aliphatic or aromatic or cycloaliphatic amines, P,P-diallyl compounds and/or P,P-di(alkylallyl) compounds and/or P-allyl-P-(alkylallyl) compounds of secondary aliphatic or aromatic or cycloaliphatic phosphines, and/or a chloride, and/or a bromide and/or an iodide of these compounds are used as monomers for the production of the anion exchange groups C.

10. The water-insoluble anion exchange materials according to claim 1, wherein diallyldimethylammonium chloride, diallylpiperidinium chloride, diallylpyrrolidinium chloride, allylmethallyldimethylammonium chloride, allylmethallylpiperidinium chloride, allylmethallylpyrrolidinium chloride, dimethallyldimethylammonium chloride, dimethallylpiperidinium chloride, dimethallylpyrrolidinium chloride, diallyl-3,4-dimethylpyrrolidinium chloride, diallyl-3,3,4,4-tetramethylpyrrolidinium chloride, diallyl-3,5-dimethylpiperidinium chloride, diallyl-3,3,5,5-tetramethylpiperidinium chloride, diallyldiphenylammonium chloride, and/or a bromide and/or an iodide of these compounds are used as monomers for the production of the anion exchange groups C.

11. The water-insoluble anion exchange materials according to claim 1, wherein diallyldimethylphosphonium chloride, diallyldiphenylphosphonium chloride, and/or a bromide and/or an iodide of these compounds are used as monomers for the production of the anion exchange groups C.

12. The water-insoluble anion exchange materials according to claim 1, in which $R_1$ is nitrogen.

13. The water-insoluble anion exchange materials according to claim 1, in which $R_2$ and/or $R_3$ are a methyl group and/or hydrogen.

14. The water-insoluble anion exchange materials according to claim 1, in which $R_4$ and $R_5$ are an alkyl group.

15. The water-insoluble anion exchange materials according to claim 1, wherein $R_4$ and $R_5$ are a methyl or ethyl group.

16. The water-insoluble anion exchange materials according to claim 1, in which $R_6$-$R_9$ are hydrogen.

17. The water-insoluble anion exchange materials according to claim 1, in which $10 \leq n \leq 50$.

18. The water-insoluble anion exchange materials according to claim 1, in which $2 \leq o \leq 10$.

* * * * *